United States Patent
Nakamura et al.

(10) Patent No.: US 10,988,496 B2
(45) Date of Patent: *Apr. 27, 2021

(54) PLATINUM (IV) COMPLEX

(71) Applicant: Nippon Kayaku Kabushiki Kaisha, Tokyo (JP)

(72) Inventors: Masaharu Nakamura, Tokyo (JP); Tsuyoshi Fukuda, Tokyo (JP); Ken Yamakawa, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/579,754

(22) PCT Filed: Jun. 16, 2016

(86) PCT No.: PCT/JP2016/067903
§ 371 (c)(1),
(2) Date: Dec. 5, 2017

(87) PCT Pub. No.: WO2016/208481
PCT Pub. Date: Dec. 29, 2016

(65) Prior Publication Data
US 2018/0179239 A1    Jun. 28, 2018

(30) Foreign Application Priority Data
Jun. 24, 2015   (JP) .............................. JP2015-126116

(51) Int. Cl.
*C07F 15/00* (2006.01)
*A61K 31/282* (2006.01)
*C07C 211/65* (2006.01)

(52) U.S. Cl.
CPC ........ *C07F 15/0093* (2013.01); *A61K 31/282* (2013.01); *C07C 211/65* (2013.01); *C07F 15/00* (2013.01)

(58) Field of Classification Search
None
See application file for complete search history.

(56) References Cited

U.S. PATENT DOCUMENTS

| | | | |
|---|---|---|---|
| 4,431,666 A | 2/1984 | Bulten et al. | |
| 4,482,569 A | 11/1984 | Bulten et al. | |
| 4,658,048 A | 4/1987 | Totani et al. | |
| 4,845,124 A | 7/1989 | Kidani et al. | |
| 5,041,578 A | 8/1991 | Khokhar | |
| 5,072,011 A | 12/1991 | Abrams et al. | |
| 5,393,909 A | 2/1995 | Khokhar et al. | |
| 5,434,256 A | 7/1995 | Khokhar et al. | |
| 6,008,395 A | 12/1999 | Kidani | |
| 9,556,214 B2 | 1/2017 | Bilodeau et al. | |
| 2001/0038830 A1 | 11/2001 | Stewart et al. | |
| 2004/0097423 A1 | 5/2004 | Siddik et al. | |
| 2004/0175387 A1 | 9/2004 | Nowotnik et al. | |
| 2006/0067910 A1 | 3/2006 | Kitagawa et al. | |
| 2006/0222696 A1 | 10/2006 | Okada et al. | |
| 2007/0148125 A1 | 6/2007 | Kataoka et al. | |
| 2007/0197427 A1 | 8/2007 | Nowotnik et al. | |
| 2011/0081404 A1 | 4/2011 | Okada et al. | |
| 2011/0110881 A1 | 5/2011 | Kataoka et al. | |
| 2014/0288244 A1 | 9/2014 | Yamamoto et al. | |
| 2014/0363491 A1 | 12/2014 | Okada et al. | |
| 2018/0250332 A1* | 9/2018 | Nakamura | ............. A61P 35/00 |
| 2019/0282612 A1 | 9/2019 | Nakamura et al. | |

FOREIGN PATENT DOCUMENTS

| | | |
|---|---|---|
| EP | 0237450 A2 | 9/1987 |
| EP | 1536864 A2 | 6/2005 |
| FR | 2954321 A1 | 6/2011 |
| JP | 61-7283 A | 1/1986 |
| JP | 62-207283 A | 9/1987 |
| JP | 1-294684 A | 11/1989 |
| JP | 3-279392 A | 12/1991 |
| JP | 5-117385 A | 5/1993 |
| JP | 3268913 B2 | 3/2002 |

(Continued)

OTHER PUBLICATIONS

Papadia et al. Int. J. Mol. Sci. 2020, 21, 2325.*
International Search Report and Written Opinion dated Sep. 20, 2016 in corresponding PCT application No. PCT/JP2016/067903.
Liu et aL, "Oxidative Addition of CI2, HCIO to Square-Planar PtII Complexes: Synthesis and Structural characterization of Platinum(II) and Platinum(IV) Bis(amidate) Complexes", European Journal of Inorganic Chemistry, 2006, pp. 1168-1173.
Misset et al., "Oxaliplatin Clinical Activity: a Review", Critical Reviews in Oncology/Hematology, vol. 35, 2000, pp. 75-93.
Ravera et al., "A New Entry to Asymmetric Platinum (IV) Complexes via Oxidative Chlorination", Inorganic chemistry, 53, 2014, pp. 9326-9335.
Wilson et al., "Synthetic Methods for the Preparation of Platinum Anticancer Complexes", Chemical Reviews, 114, 2014, pp. 4470-4495.

(Continued)

*Primary Examiner* — Clinton A Brooks
(74) *Attorney, Agent, or Firm* — Nields, Lemack & Frame, LLC

(57) ABSTRACT

According to the present invention, there is a demand for novel platinum(IV) complex which has sufficient water-solubility, stability, antitumor activity, and the like that are required as a medicine, and may be used clinically. Thus, provided is a platinum(IV) complex represented by the following General Formula (I) [wherein $X_1$ and $X_2$ each represent a halogen atom or are bonded together to form a dicarboxylate selected from the group consisting of oxalate, malonate, succinate, and o-phthalate; and Y represents a halogen atom.

(I)

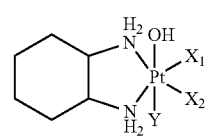

4 Claims, 1 Drawing Sheet

(56) References Cited

FOREIGN PATENT DOCUMENTS

| | | | |
|---|---|---|---|
| JP | 2006-504691 A | 2/2006 | |
| JP | 3955992 B2 | 8/2007 | |
| JP | 2008-538105 A | 10/2008 | |
| JP | 2011-105792 A | 6/2011 | |
| JP | 2011-137046 A | 7/2011 | |
| JP | 4745664 B2 | 8/2011 | |
| JP | 5458255 B2 | 4/2014 | |
| SU | 1186617 A1 | 10/1985 | |
| WO | 90/05734 A1 | 5/1990 | |
| WO | 96/26949 A1 | 9/1996 | |
| WO | 2004/024062 A2 | 3/2004 | |
| WO | 2005/056641 A1 | 6/2005 | |
| WO | 2011/058776 A1 | 5/2011 | |
| WO | 2014/100417 A1 | 6/2014 | |

OTHER PUBLICATIONS

Office action dated Dec. 26, 2018 in co-pending U.S. Appl. No. 15/759,295.

Xu et al., "Mono- and Di-Bromo Platinum(IV) Prodrugs via Oxidative Bromination: Synthesis, Characterization, and cytotoxicity," Dalton Transactions, vol. 44, No. 46, pp. 19918-19926, 2015.

European communication dated Feb. 12, 2019 in corresponding European patent application No. 16814252.9.

Russian communication, with English translation, dated Mar. 29, 2019 in corresponding Russian patent application No. 2017140223/04.

European communication dated Mar. 28, 2019 in co-pending European patent application No. 16846368.5.

Notice of allowance dated Aug. 12, 2019 in co-pending U.S. Appl. No. 15/759,295.

International Search Report and Written Opinion dated Nov. 22, 2016 in co-pending PCT application No. PCT/JP2016/076482.

Du et al., "Nanoparticle delivery of photosensitive Pt(IV) drugs for circumventing cisplatin cellular pathway and on-demand drug release", Colloids and Surfaces B: Biointerfaces, vol. 123, pp. 734-741, 2014.

Graf et al., "Platinum(IV)-chlorotoxin (CTX) conjugates for targeting cancer cells", Journal of Inorganic Biochemistry, vol. 110, pp. 58-63, 2012.

Hall et al., "Basis for Design and Development of Platinum(IV) Anticancer Complexes", Journal of Medical Chemistry, vol. 50, No. 15, pp. 3403-3411, Jul. 26, 2007.

Hou et al., "A Core Cross-Linked Polymeric Micellar Platinum(IV) Prodrug with Enhanced Anticancer Efficiency", Macromolecular Bioscience, vol. 13, pp. 954-965, 2013.

Jehn et al., "Pharmacokinetics of Liposomal Cisplatin (Lipoplatin) in Combination with 5-FU in Patients with Advanced Head and Neck Cancer: First Results of a Phase III Study", Anticancer Research, vol. 27, pp. 471-475, 2007.

Scarano et al., "Folate Conjugation to Polymeric Micelles via Boronic Acid Ester to Deliver Platinum Drugs to Dvarian Cancer Cell Lines", Biomacromolecules, vol. 14, pp. 962-975, 2013.

Shanmugam et al., "Oligonucleotides—Assembled Au Nanorod-Assisted Cancer Photothermal Ablation and Combination Chemotherapy with Targeted Dual-Drug Delivery of Doxorubicin and Cisplatin Prodrug", ACS Applied Materials & Interfaces, vol. 6, pp. 4382-4393, 2014.

Wang et al., "Co-Delivery of Oxaliplatin and Demethylcantharidin via a Polymer-Drug Conjugate", Macromolecular Bioscience, vol. 14, pp. 588-596, 2014.

Xiao et al., "Co-delivery of daunomycin and oxaliplatin by biodegradable polymers for safer and more efficacious combination therapy", Journal of Controlled Release, vol. 163, pp. 304-314, 2012.

Xiao et al., "A prodrug strategy to deliver cisplatin(IV) and paclitaxel in nanomicelles to improve efficacy and blerance", Biomaterials, vol. 33, pp. 6507-6519, 2012.

Xiao et al., "Biodegradable polymer cisplatin(IV) conjugate as a pro-drug of cisplatin(II)", Biomaterials, vol. 32, pp. 7732-7739, 2011.

Zheng et al., "Pt(IV) Prodrugs Designed to Bind Non-Covalently to Human Serum Albumin for Drug Delivery", Journal of the American Chemical Society, vol. 136, pp. 8790-8798, 2014.

Office action dated Oct. 31, 2018 in co-pending U.S. Appl. No. 15/759,295.

Office action dated Sep. 17, 2019 in co-pending U.S. Appl. No. 16/431,811.

European communication dated Nov. 22, 2019 in corresponding European patent application No. 16814252.9.

Notice of allowance dated Nov. 18, 2019 in co-pending U.S. Appl. No. 15/759,295.

Chinese communication, with English translation, dated Sep. 16, 2019 in corresponding Chinese patent application No. 201680035654.5.

Taiwanese communication, with English translation, dated Oct. 5, 2019 in corresponding Taiwanese patent application No. 105119624.

Indian communication dated Oct. 25, 2019 in corresponding Indian patent application No. 201817000967.

Wexselblatt et al., "Platinum (IV) Prodrugs with Haloacetato Ligands in the Axial Positions can Undergo Hydrolysis Under Biologically Relevant Conditions", Angewandte Chemie, vol. 52, Iss. 23, pp. 6059-6062, May 2013.

Office action dated May 28, 2020 in co-pending U.S. Appl. No. 16/431,811.

Chinese communication, with English translation, dated May 28, 2020 in corresponding Chinese patent application No. 201680035654.5.

Japanese communication, with English translation, dated Jun. 2, 2020 in corresponding Japanese patent application No. 2017-525288.

Brazilian communication, with English translation, dated Nov. 17, 2020 in co-pending Brazilian patent application No. BR112018003530-0.

Notice of allowance dated Mar. 5, 2021 in co-pending U.S. Appl. No. 16/431,811.

* cited by examiner

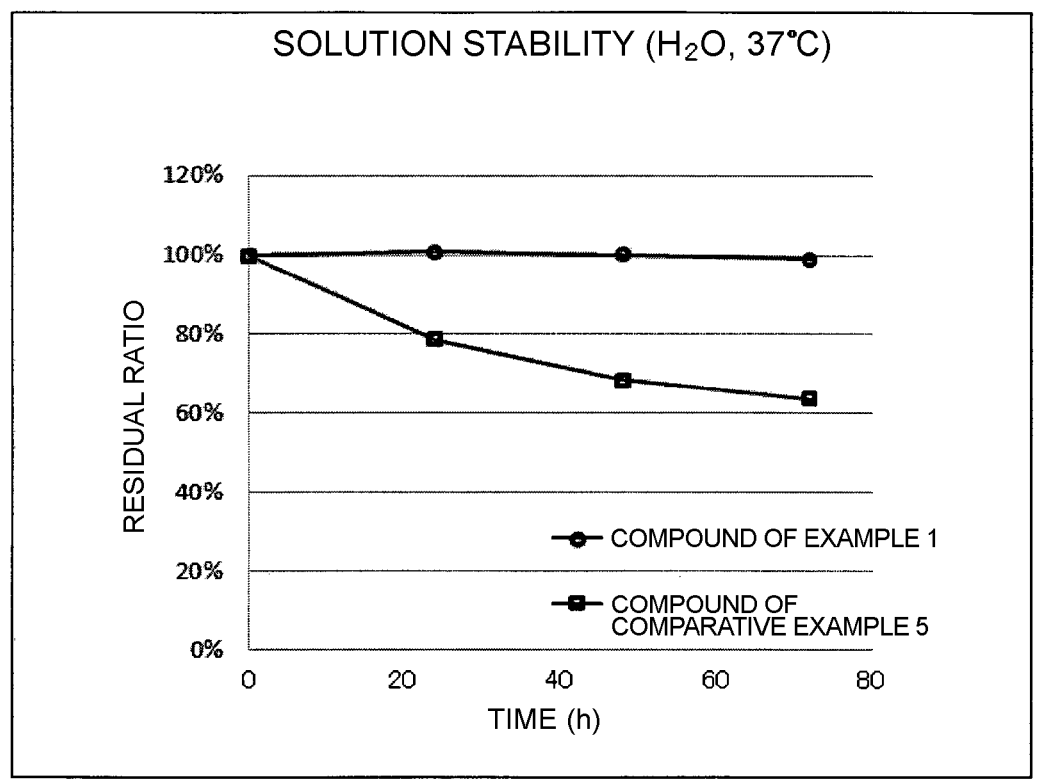

PLATINUM (IV) COMPLEX

TECHNICAL FIELD

The present invention relates to a novel platinum(IV) complex and a medicine containing the complex as an active ingredient.

BACKGROUND ART

Cisplatin is a platinum(II) complex having a broad anticancer spectrum and strong antitumor activity, and cisplatin is used for the treatment of various cancers as a core drug for combination chemotherapy in cancer chemotherapy. However, it is known that kidney disorder, nausea, and vomiting occur as adverse drug reactions, and countermeasures need to be taken at the time of use. Furthermore, the emergence of cells having resistance to cisplatin has posed a problem in the clinical use of cisplatin.

Regarding other platinum(II) complexes that are clinically used, oxaliplatin is used for the treatment of colorectal cancer and the like. However, it is known that peripheral nerve disorder and the like occur as adverse drug reactions, and this has posed a problem in the treatment. Meanwhile, it is believed that oxaliplatin does not show cross-resistance with cisplatin, and it is considered that it is important for oxaliplatin to have a ligand having an amine structure that is different from that of cisplatin, that is, a ligand having a 1,2-cyclohexanediamine (hereinafter, may be abbreviated to dach) structure (see Non Patent Literature 1).

Regarding platinum complexes that have anticancer activity, platinum(IV) complexes are known in addition to platinum(II) complexes. A feature of the platinum(IV) complexes is that changes in the physical properties such as water-solubility occurring as a result of converting the ligands at the axial positions to various substituents, enhancement of activity as a result of binding of targeting molecules to targets, and the like may be expected (see Non Patent Literature 2).

Regarding platinum(IV) complexes having a ligand having the dach structure as in the case of oxaliplatin, for example, a complex having two halogen atoms at the axial positions (see Patent Literature 1), a complex having a halogen atom and a carboxylate at the axial positions (see Patent Literature 2), a complex having a halogen atom and a substituted alkoxy group at the axial positions (see Patent Literature 3), and a complex having two carboxylates at the axial positions (see Patent Literature 4) are known.

Furthermore, Non Patent Literature 3 and Non Patent Literature 4 describe platinum(IV) complexes having a halogen atom and a hydroxyl group at the axial positions. However, a compound having both a ligand having the Each structure and a leaving group of an oxalate structure or a halogen atom is not described in the literatures.

Clinical studies on satraplatin, tetraplatin, iproplatin, and the like (see Non Patent Literature 2), which are platinum (IV) complexes, have been hitherto attempted; however, development thereof has been suspended. Thus, there is a demand for a novel platinum(IV) complex having high efficacy.

Prior Art Literature(s)

Patent Literature(s)

Patent Literature 1: WO 90/05734 A1
Patent Literature 2: WO 96/26949 A1
Patent Literature 3: FR 2954321 A1
Patent Literature 4: WO 2014/100417 A1

Non Patent Literature(s)

Non Patent Literature 1: Critical Reviews in Oncology: Hematology, 2000, 35, 75-93
Non Patent Literature 2: Chemical Reviews, 2014, 114, 4470-4495
Non Patent Literature 3: Inorganic Chemistry, 2014, 53, 9326-9335
Non Patent Literature 4: European Journal of inorganic Chemistry, 2006, 1168-1173

SUMMARY OF INVENTION

Problem to be Solved

There is no platinum(IV) complex which sufficiently exhibits water-solubility, stability, and antitumor effects at levels that are required as medicines, and there is a demand for a novel platinum(IV) complex that may be clinically used.

Means to Solve The Problem

The present inventors conducted a thorough intensive studies in order to solve the problems described above, and as a result, the inventors found that when a halogen atom and a hydroxyl group are selected as the axial ligands for a platinum(IV) complex having a ligand with the Bach structure, a complex which has excellent antitumor activity, and which is chemically stable, and which has excellent solubility is obtained. Thus, the inventors completed the present invention.

That is, the present invention relates to the following (1) to (4).

(1) A platinum(IV) complex represented by the following General Formula (I):

[Chemical Formula 1]

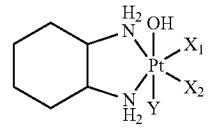

wherein $X_1$ and $X_2$ both represent a halogen atom, or are bonded together to represent a dicarboxylate selected from the group consisting of oxalate, malonate, succinate, and o-phthalate; and Y represents a halogen atom.

(2) The platinum(IV) complex according to item (1), wherein $X_1$ and $X_2$ both represent a chlorine atom or a bromine atom, or are bonded together to represent an oxalate; and Y represents a chlorine atom or a bromine atom.

(3) The platinum(IV) complex according to (1) or (2), wherein the 1,2-cyclohexanediamine ligand is a (1R,2R)-cyclohexanediamine ligand.

(4) A medicine including the platinum(IV) complex according to any one of (1) to (3), as an active ingredient.

Effects of Invention

According to the present invention, a platinum(IV) complex having excellent antitumor activity and having wafersolubility with chemical stability, and a medicine including the complex as an active ingredient, may be provided.

BRIEF DESCRIPTION OF DRAWINGS

FIG. 1 is a diagram illustrating the results of Test Example 3, which is a test assessing the stability of the compound of Example 1 and the compound of Comparative Example 5 in an aqueous solution at 37° C.

DETAILED DESCRIPTION OF THE INVENTION

Hereinafter, the details of the present invention will be described.

The halogen atom according to the present invention is a fluorine atom, a chlorine atom, a bromine atom, or an iodine atom. It is preferable that $X_1$ and $X_2$ both represent the same halogen atom, and above all, it is particularly preferable that $X_1$ and $X_2$ both represent a chlorine atom or a bromine atom. Y is preferably a chlorine atom or a bromine atom.

The dicarboxylate, which is a leaving group, according to the present invention is not particularly limited, and examples include a (C1-C6) alkyl group having two carboxyl groups, and a (C6-C10) aryl group having two carboxyl groups. Among them, oxalate, malonate, succinate, and o-phthalate shown below are preferred.

[Chemical Formula 2]

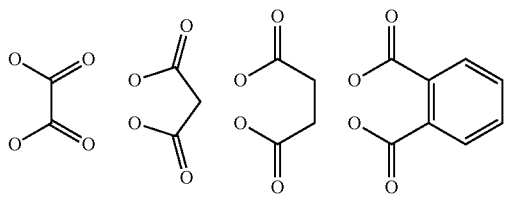

The platinum complex of the present invention is particularly preferably a compound represented by the following General Formula (II) or General Formula (IV).

[Chemical Formula 3]

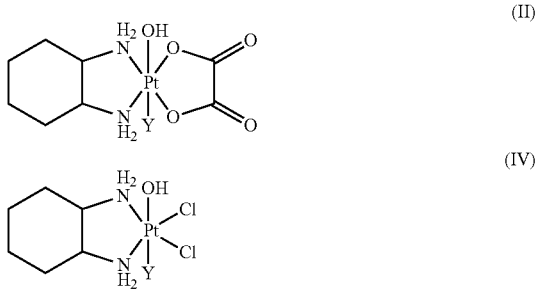

wherein Y represents a halogen atom.

Regarding the steric structure of the 1,2-cyclohexanediamine ligand of the platinum(IV) complex of the present invention, (1R, 2R)-trans disposition is preferred from the viewpoint of physiological activity or the like.

That is, the platinum(IV) complex of the present invention is particularly preferably a compound represented by the following General Formula (III) or General Formula (V).

[Chemical Formula 4]

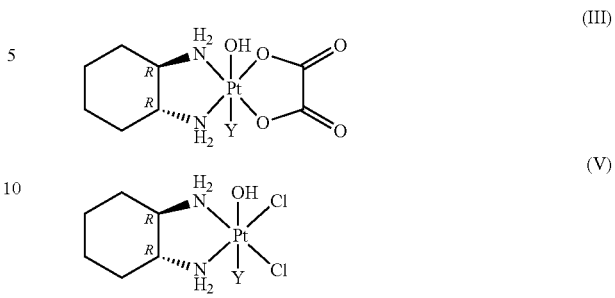

wherein Y represents a halogen atom.

The platinum(IV) complex of the present invention may be produced by applying methods described is the literature such as Non Patent Literature 2. That is, a method of treating a platinum(II) complex with an oxidizing agent such as hydrogen peroxide, or subjecting a platinum(II) complex to an oxidative halogenation, and thereby obtaining an intended platinum(IV) complex; or a method of subjecting a platinum(IV) complex to a substitution reaction, and thereby obtaining an intended platinum(IV) complex, may be used. Examples of these production methods are described in the following Examples.

A medicine including the platinum(IV) complex of the present invention as an active ingredient is also included in the present invention. The pharmaceutical application in which the platinum(IV) complex of the present invention exhibits efficacy is not particularly limited; however, a use application as an anticancer agent is preferred. Regarding the use as an anticancer agent, the platinum(IV) complex may be used alone, or may be mixed with pharmaceutically acceptable additives such as a carrier, an excipient, a disintegrant, a binder, a lubricating agent, a fluidizing agent, a coating agent, a suspending agent, an emulsifier, a stabilizer, a preservative, a flavoring agent, a fragrance, a diluents, and a dissolution aid. The anticancer agent may be administered orally or parenterally (systemic administration, topical administration, or the like) in the form of preparations such as a powder preparation, a granular preparation, a tablet, a caplet, a capsule, an injectable preparation, a suppository, and an ointment. The platinum(IV) complex of the present invention in the preparation may vary widely depending on the preparation; however, the proportion is usually 0.1% to 100% by weight. The dose may vary depending on the route of administration, the age of the patient, the actual symptoms to be prevented or treated, and the like; however, for example, in the case of administering the preparation to an adult, the platinum(IV) complex may be administered, as an active ingredient, at a dose of 0.01 mg to 2,000 mg, and preferably 0.1 mg, to 1,000 mg, per day, and may be administered once a day or in several divided portions a day.

EXAMPLES

Hereinafter, the present invention will be described in more detail by way of Examples. However, the present invention is not intended to be limited to these Examples.

In the Examples of the present invention, the following abbreviations will be used.

ox: oxalate
cbdc: 1,1-cyclobutanedicarboxylate
l-OHP: oxaliplatin

Measurement of the purity of compounds in the present Example was carried out by using high performance liquid chromatography and using L-column2 ODS (4.6 mm I.D.× 250 mm; purchased from Chemicals Evaluation and Research Institute, Japan) as a column; a buffer solution prepared by dissolving 2.72 g of potassium dihydrogen phosphate, 1.89 g of sodium 1-pentanesulfonate, and 0.5 ml of triethylamine in 2,000 ml of distilled water and adjusting the solution to pH 4.3 with phosphoric acid, as a mobile phase (A); and methanol as a mobile phase (B), under the following analysis conditions 1 or 2.

Analysis Conditions 1 (Isocratic Analysis):
Mobile phase (B) concentration: 15% (0 min) to 15% (20 min)
Mobile phase flow rate: 1 ml/min, detection: 210 nm
Analysis Conditions 2 (Gradient Analysis):
Mobile phase (3) concentration: 15% (0 min) to 90% (10 min)
Mobile phase flow rate: 1 ml/min, detection 210 nm.

Example 1

Synthesis of trans,cis,cis-[PtCl(OH) (R,R-dach) (ox)]: Y=Cl in General Formula (III)

N-chlormide (66.8 mg) was dissolved in 14 ml of distilled water, and a liquid obtained by suspending 1-OHP (200 mg) in 6 ml of distilled water was added thereto. The mixture thus obtained was stirred for 4 hours at room temperature in the dark. After completion of the reaction, insoluble materials in the reaction liquids were separated by filtration, the filtrate was concentrated under reduced pressure, and thereby a solid was obtained. The solid thus obtained was recrystallized from ethanol/water, and thus the title compound (114 mg) was obtained. $^1$H-NMR ($D_2O$): δ 2.89-2.72 (2H, m), 2.15 (2H, d, J=12.2 Hz), 1.53-1.41 (4H, m), 0.97-0.90 (2H, m), MS (ESI; Electrospray Ionization): 450 (M+1), 451 (M+2), purity (HPLC, analysis conditions 2): 99.4%.

Example 2

Synthesis of trans,cis,cis-[PtBr(OH) (R,R-dach) (ox)]: Y=Br in General Formula (III)

N-bromosuccinmide (89.6 mg) was dissolved in 14 ml of distilled water, a liquid obtained by suspending 1-OHP (200 mg) in 6 ml of distilled water was added thereto. The mixture thus obtained was stirred for 3 hours at room temperature in the dark. After completion of the reaction, insoluble materials in the reaction liquid were separated by filtration, the filtrate was concentrated under reduced pressure, and thereby a solid was obtained. The solid thus obtained was suspended in water and collected by filtration again, and thus the title compound (216 mg) was obtained. $^1$H-NMR (DMSO-$d_6$): δ 7.91-7.65 (2H, m) 7.14-7.03 (2H, m), 2.65-2.55 (2H, m), 2.07-1.94 (2H, m), 1.50-1.46 (4H, m), 1.15-1.02 (2H, m), MS (ESI): 495 (M+1), purity (HPLC, analysis conditions 2): 98.9%.

Example 3

Synthesis of trans,cis,cis-[PtCl(OH) (R,R-dach) (Cl)$_2$]: $X_1$, $X_2$, Y=Cl in General Formula (I)

N-chlorosuccinimide (105.4 mg) was dissolved in 7 ml of distilled water, the solution was added to a liquid obtained by suspending Pt (R,R-dach) Cl$_2$ (300 mg) in 60 ml of tetrahydrofuran. The mixture thus obtained was stirred for 4 hours at room temperature in the dark. After completion of the reaction, insoluble materials in the reaction liquid were separated by filtration, the filtrate was concentrated under reduced pressure, and thereby a solid was obtained. The solid thus obtained was suspended in ethanol and collected by filtration again, and thus the title compound (322 mg) was obtained. $^1$H-NMR (DMSO-$d_6$): δ 7.53-7.29 (2H, m), 6.89-6.78 (2H, m), 2.75-2.60 (2H, m), 2.10-2.00 (2H, m), 1.47 (2H, d, J=8.0 Hz), 1.10-0.93 (2H, m), MS (PSI): 433 (M+1), purity (HPLC, analysis conditions 2): 98.1%.

Comparative Example 1

Synthesis of trans,cis,cis-[Pt(OH)(OAc)(R,R-dach) (ox)]

0.135 ml of a 30% aqueous solution of hydrogen peroxide was added to a liquid obtained by suspending 1-OHP (200 mg) in 9 ml of acetic acid. The mixture thus obtained was stirred for 19 hours at room temperature in the dark. After completion of the reaction, the mixture was concentrated under reduced pressure several times while water added thereto, and thus a solid was obtained. The solid thus obtained was recrystallized from ethanol/methanol, and thus the title compound (55 mg) was obtained. $^1$H-NMR ($D_2O$): δ 2.78-2.73 (2H, m), 2.17 (2H, d, J=9.2 Hz), 1.94 (3H, s), 1.54-1.44 (4H, m), 1.20-1.05 (2H, m) purity (HPLC, analysis conditions 1): 94.0).

Comparative Example 2

Synthesis of trans,cis,cis-[PtCl (OCH$_2$CH$_2$OH) (R,R-dach) (ox)]

N-chlorosuccinimide (66.8 mg) was added to a liquid obtained by suspending 1-OHP (200 mg) in 2 ml of ethylene glycol. The mixture thus obtained was stirred for 3 hours at room temperature in the dark. After completion of the reaction, 10 ml of acetone and 30 ml of diethyl ether were added to the reaction liquid, and a solid precipitated therefrom was collected by filtration. The solid thus obtained was recrystallized from ethanol/water, and thus the title compound (154 mg) was obtained. $^1$H-NMR ($D_2O$): 53.58-3.45 (2H, m), 3.22-3.08 (2H, m), 2.85-2.83 (2H, m), 2.14 (2H, d, J=11.2 Hz), 1.53-1.44 (4H, m), 1.15-1.07 (2H, m), purity (HPLC, analysis conditions 1): 98.0%.

Comparative Example 3

Synthesis of trans,cis,cis-[Pt(OH)$_2$ (R,R-dach) (ox)]

2.58 ml of a 30% aqueous solution of hydrogen peroxide was added to a liquid obtained by suspending 1-OHP (900 mg) in 12 ml of distilled water. The mixture thus obtained was stirred for 20.5 hours at room temperature in the dark. After completion of the reaction, the mixture was concentrated under reduced pressure several times while water was added thereto, and a solid was obtained. The solid thus obtained was recrystallized from distilled water, and thereby the title compound (422 mg) was obtained. $^1$H-NMR ($D_2O$): δ 2.74-2.72 (2H, m), 2.17 (2H, d, J=12.8 Hz), 1.54-1.45 (4H, m), 1.18-1.12 (2H, m), purity (HPLC, analysis conditions 1): >98.0%.

Comparative Example 4

Synthesis of trans,cis,cis-[Pt(OCOCH$_2$CH$_2$C$_6$H$_5$)$_2$(R,R-dach)(ox)]

3-Phenylpropionic acid (77 mg) and N,N-dimethylaminopyridine (5.7 mg) were dissolved in 2 ml of N,N-dimethylformamide, 0.086 ml of diisopropylcarbodiimide was added thereto, and then the mixture was stirred for 0.5 hours at room temperature. To the reaction liquid, a liquid obtained by suspending trans,cis,cis-[Pt(OH)$_2$ (R,R-dash)(ox)] (200 mg) obtained in Comparative Example 3 in 2 ml of N,N-dimethylformamide was added. The mixture thus obtained was stirred for 23 hours at room temperature in the dark. The reaction liquid was filtered to exclude any unreacted platinum complex, and a solid was precipitated by adding water to the filtrate thus obtained. The solid was collected by filtration and was washed with cold ethanol, and thus the title compound (38 mg) was obtained. $^1$H-NMR (DMSO-d$_6$): δ 8.30 (4H, brs), 7.27-7.14 (10H, m), 2.80-2.76 (4H, m), 2.60-2.56 (4H, m), 2.40-2.30 (2H, m), 2.05 (2H, d, J=12.4 Hz), 1.47 (2H, d, J=8.0 Hz), 1.40-1.22 (2H, m), 1.15-1.14 (2H, m), purity (HPLC, analysis conditions 2): 98.0%.

Comparative Example 5

Synthesis of trans,cis,cis-[PtCl(OH) (R,R-dach)(cbdc)]

The title compound was synthesized according to the method described in Non Patent Literature 3. $^1$H-NMR (DMSO-d$_6$): δ 7.71-7.43 (2H, m), 7.00-6.90 (2H, m), 2.60-2.29 (6H, m), 2.03-1.93 (2H, m), 1.84-1.49 (2H, m), 1.50-1.30 (4H, m), 1.05-0.95 (2H, m), MS (ESI): 504 (M+1), 486 (M+OH), purity (HPLC, analysis conditions 2): 95.6%.

Comparative Example 6

Synthesis of trans,cis,cis-[Pt(OH)$_2$(R,R-dach)(cbdc)]

Cis,cis-[Pt(R,R-dach) (cbdc)] (100 mg) synthesized according to the method described in Non Patent Literature 3 was dissolved in 14 ml of a 50% acetone solution, 14 ml of a 30% aqueous solution of hydrogen peroxide was added thereto. The mixture thus obtained was stirred for 4 hours at room temperature in the dark. After completion of the reaction, the mixture was concentrated under reduced pressure several times while water was added thereto, and a solid was obtained. The solid thus obtained was suspended and purified in acetone, and thus the title compound (41 mg) was obtained. $^1$H-NMR (D$_2$O): 2.97 (2H, d, J=10.0 Hz), 2.77-2.72 (4H, m), 2.36-2.32 (2H, m), 2.14-2.10 (2H, m), 1.74-1.64 (4H, m) 1.37-1.34 (2H, m), MS (ESI): 486 (M+1), 486 (M−OH), purity (HPLC, analysis conditions 2): 96.8%.

Test Example 1

In Vitro Antitumor Assay for Example Compounds and Comparative Example Compounds Gastric cancer and pancreatic cancer cell lines were respectively inoculated on a 96-well plate. Gastric cancer cells KATO III were inoculated at a rate of 1×10$^4$ cells/well, gastric cancer cells MKN-1 were inoculated at a rate of 5×10$^5$ cells/well, gastric cancer cells MKN-45 were inoculated at a rate of 1×10$^4$ cells/well, gastric cancer cells MKN-74 were inoculated at a rate of 1×10$^4$ cells/well, pancreatic cancer cells AsPC-1 were inoculated at a rate of 5×10$^7$ cells/well, pancreatic cancer cells BxPC-3 were inoculated at a rate of 5×10$^5$ cells/well, pancreatic cancer cells DAN-G were inoculated at a rate of 5×10$^5$ cells/well, and pancreatic cancer cells SUIT-2 were inoculated at a rate of 5×10$^5$ cells/well. After culturing the cells for 24 hours, each of the Example compounds or each of the Comparative Example compounds was added to the cells to obtain a final concentration of from 0.0244 μmol/L to 100 μmol/L at a common ratio of 4. Three technical replicates were used. Wells to which no drug was added were prepared as control, and wells to which cells and drugs were not added were prepared as blanks. After the cells were cultured for 72 hours, the culture fluid was removed, the cells were fixed with methanol, and then the cells were stained using a Methylene Blue stain solution. After excess Methylene blue stain solution was washed off, 200 μL of 0.1% hydrochloric acid was added to each well, and the dye was extracted. The light absorbance at 660 nm was measured using a microplate reader, and the cell proliferation inhibitory activity (GI %) was calculated from the light absorbance thus obtained by the following formula.

$$GI_{XY}\% = (1-(A_{XY}-B)/(C-B))\times 100$$

Here, GI$_{XY}$% represents the cell prolj feration-inhibitory activity when the concentration of compound. X is Y μM; A$_{XY}$ represents the average light absorbance of the well to which compound X has been added at Y μM; B represents the light absorbance of a blank well; and C represents the tight absorbance of a control well.

The GI$_{XY}$% was determined for various compound concentrations, and a proliferation-inhibition curve was plotted from the concentration and the cell proliferation-inhibitory activity. Thus, the concentration at which the cell proliferation-inhibitory activity was 50% was designated as the IC$_{50}$ value of compound X. The results are presented in Tables 1, 2, and 3.

TABLE 1

| | Axial ligand | | Cell line IC$_{50}$ (μM) | | | |
|---|---|---|---|---|---|---|
| | Y | X$_1$, X$_2$ | KATO III | MKN-1 | MKN-45 | MKN-74 |
| Compound of Example 1 | OH, Cl | ox | 13.8 | 1.9 | 0.3 | 16 |
| Compound of Comparative Example 1 | OH, OAc | ox | 55.7 | 45.3 | 6.2 | >100 |
| Compound of Comparative Example 2 | OC$_3$H$_4$OH, Cl | ox | 42.6 | 10.8 | 1.9 | 58.1 |
| Compound of Comparative Example 3 | OH, OH | ox | n.t | >100 | n.t | >100 |
| Compound of Comparative Example 4 | OCOR, OCOR | ox | n.t | 9.2 | n.t | 27.3 |
| 1-OHP | — | ox | 9.2 | 0.5 | 0.1 | 8.6 |
| Pt(dach)Cl$_2$ | — | Cl, Cl | 13.8 | 3.7 | 0.5 | 22.3 |

R represents CH$_2$CH$_2$C$_6$H$_5$.
n.t stands for "not tested".

TABLE 2

|  | Axial ligand | | Cell line IC$_{50}$ (μM) | | | |
| --- | --- | --- | --- | --- | --- | --- |
|  | Y | X$_1$, X$_2$ | BxPC-3 | SUIT-2 | DAN-G | AsPC-1 |
| Compound of Example 1 | OH, Cl | ox | 1.2 | 0.9 | 1 | 3.1 |
| Compound of Comparative Example 1 | OH, OAc | ox | 44.3 | 26.1 | 36.7 | 62.9 |
| Compound of Comparative Example 2 | OC$_3$H$_4$OH, Cl | ox | 5.7 | 6.1 | 5.6 | 9.7 |
| Compound of Comparative Example 3 | OH, OH | ox | n.t | 39.2 | >100 | n.t. |
| Compound of Comparative Example 4 | OCOR, OCOR | ox | n.t | 1 | 6.8 | n.t. |
| l-OHP | — | ox | 0.8 | 0.4 | 1.1 | 1.6 |
| Pt(dach)Cl$_2$ | — | Cl, Cl | 3.4 | 2.1 | 8.5 | 14.7 |

R represents CH$_2$CH$_2$C$_6$H$_5$.

Example 1 compound exhibited high antitumor effects against all cell lines, compared to the compounds of Comparative examples 1 to 4, in which the combinations of the axial ligands were different. From this, it became clear that regarding the combination of axial ligands in a platinum(IV) complex having the dach structure, the combination of a hydroxyl group and a halogen atom of the compound of Example 1 was excellent. Meanwhile, the compound of Example 1 exhibited an activity equivalent to that of l-OHP that is used as an anticancer agent, and exhibited higher activity compared to Pt (dach) Cl$_2$.

TABLE 3

|  | Ligand | | Cell line IC$_{50}$ (μM) | | | |
| --- | --- | --- | --- | --- | --- | --- |
|  | Axial | X$_1$, X$_2$ | MKN-1 | MKN-74 | SUIT-2 | DAN-G |
| Compound of Example 1 | OH, Cl | ox | 1.9 | 16 | 0.9 | 1 |
| Compound of Example 2 | OH, Br | ox | 2.7 | n.t. | 1.5 | n.t. |
| Compound of Example 3 | OH, Cl | Cl, Cl | 2.6 | 17.1 | 0.9 | 8.6 |
| Compound of Comparative Example 3 | OH, OH | ox | >100 | >100 | 39.2 | >100 |
| Compound of Comparative Example 5 | OH, Cl | cbdc | 4.5 | 29 | 3.3 | 3.4 |
| Compound of Comparative Example 6 | OH, OH | cbdc | >100 | >100 | 79.4 | >100 |
| l-OHP | — | ox | 0.5 | 8.6 | 8.4 | 1.1 |

Although the compounds of Comparative Examples 5 and 6 had inferior activity compared to the compounds of the present invention, it became clear from the results for the compound of Comparative Example 5 and the compound of Comparative Example 6 that even in a case in which X$_1$ and X$_2$ were converted to cbdc, regarding the combination of the axial ligands of the platinum(IV) complex having the dach structure, the combination of a hydroxyl group and a chlorine atom or a bromine atom is excellent. Furthermore, it became clear from the results for the compound of Example 3 that a combination in which Y represents a chlorine atom, and X$_1$ and X$_2$ both represent a chlorine atom also exhibits high antitumor activity.

Test Example 2

Test on Solubility in Water of Compound of Example 1 and Compound of Comparative Example 5

The compound of Example 1 and the compound of Comparative Example 5 were weighed, distilled water was slowly added to each of the compounds, and thereby the concentration at which crystals were completely dissolved was measured. The results are presented in Table 4. The solubility of l-OHP is the reference value calculated from the literature value.

TABLE 4

|  | Solubility (mg/ml) |
| --- | --- |
| Compound of Example 1 | 7 |
| Compound of Comparative Example 5 | 3 |
| l-OHP | 2-2.5 |

As a result, it became clear that the solubility in water of the compound of Example 1, which is a platinum(IV) complex having a hydroxyl group and a halogen atom introduced thereinto as the axial ligands of the present invention, increased by about 3 times the solubility of 1-OHP, which is a corresponding platinum(II) complex. Furthermore, the solubility was higher by two times or more than that of the compound of Comparative Example 5, which is an existing platinum(IV) complex.

Test Example 3

Test on Solution Stability in Distilled Water of Compound of Example 1 and Compound of Comparative Example 5

The compound of Example 1 and the compound of Comparative Example 5 were weighed in a vessel, and the compounds were dissolved to a concentration of 1 mg/ml using distilled water. Each of the aqueous solutions was filtered using a syringe filter having a pore size of 0.45 μm, and the filtrate was shaken in a water bath at 37° C. in the dark. Sampling was performed over time, and stability was tested by high performance liquid chromatography. The results are presented in FIG. 1.

As a result of the test, the residual ratio of the compound of Example 1 after 74 hours was 99.1%, while the residual ratio of the compound of Comparative Example 5, which is an existing platinum(IV) complex, was 63.7%. It is obvious that the compound of Example 1 of the present invention was stable for a long time period in an aqueous solution and was stable even compared to the compound of Comparative Example 5.

Test Example 4

Test on Solution Stability Physiological Saline of Compound of Example 1

The compound of Example 1 was weighed in a vessel, and the compound was dissolved to a concentration of 1 mg/ml using physiological saline. The solution was allowed to stand at 5° C. in the dark or was shaken in a water bath at 37° C. without blocking light, and the residual amount was quantitatively determined by high performance liquid chromatography. The residual ratio is presented in Table 5.

TABLE 5

| | | Residual ratio | |
|---|---|---|---|
| | Conditions | 3 hours | 24 hours |
| Compound of Example 1 | 5° C., in the dark, allowed to stand | 100% | 98.77% |
| Compound of Example 1 | 37° C., without blocking light, shaken | 100% | 94.43% |

Generally, a platinum complex having a leaving group other than a chlorine atom, for example, 1-OHP, undergoes exchange of chlorine ions in physiological saline, and therefore, the platinum complex is unstable in physiological saline. However, as shown by the results of the present test, the compound of Example 1 of the present invention, which is a platinum(IV) complex having a dicarboxylate as a leaving group, almost does not undergo decomposition after 24 hours at 5° C. in the dark even in physiological saline. Even though the compound of Example 1 was shaken at 37° C. without blocking light, which constituted more severe conditions, the residual ratio was 94.4%, and the compound was stable even in physiological saline.

From the various test results described above, it has become clear that the platinum complex of the present invention has excellent antitumor activity and excellent solubility, and has excellent performance that even if the platinum complex is produced into a solution, the platinum complex is chemically stable.

The invention claimed is:

1. An isolated platinum(IV) complex of the following General Formula (I):

[Chemical Formula 1]

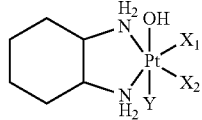

(I)

wherein $X_1$ and $X_2$ form oxalate and Y represents a chlorine atom or a bromine atom.

2. The isolated platinum(IV) complex according to claim 1, wherein the 1,2-cyclohexanediamine ligand is a (1R,2R)-cyclohexanediamine ligand.

3. A medicine comprising the isolated platinum(IV) complex according to claim 1 as an active ingredient.

4. A medicine comprising the isolated platinum(IV) complex according to claim 2 as an active ingredient.

* * * * *